United States Patent
Conti et al.

(10) Patent No.: US 9,220,726 B2
(45) Date of Patent: Dec. 29, 2015

(54) COMBINATION FOR THE TREATMENT OF RADIATION- OR CHEMOTHERAPY-INDUCED MUCOSITIS

(71) Applicant: PROFESSIONAL DIETETICS S.R.L., Milan (IT)

(72) Inventors: Franco Conti, Milan (IT); Francesco Saverio Dioguardi, Milan (IT)

(73) Assignee: PROFESSIONAL DIETETICS S.R.L., Milan (IT)

( * ) Notice: Subject to any disclaimer, the term of this patent is extended or adjusted under 35 U.S.C. 154(b) by 8 days.

(21) Appl. No.: 14/553,897

(22) Filed: Nov. 25, 2014

(65) Prior Publication Data
US 2015/0079009 A1    Mar. 19, 2015

Related U.S. Application Data

(63) Continuation of application No. 13/511,900, filed as application No. PCT/EP2010/068216 on Nov. 25, 2010.

(30) Foreign Application Priority Data

Nov. 26, 2009 (IT) .............................. MI2009A2080

(51) Int. Cl.
| | | |
|---|---|---|
| *A61K 31/728* | (2006.01) | |
| *A61K 31/198* | (2006.01) | |
| *A61K 31/401* | (2006.01) | |
| *A61K 31/138* | (2006.01) | |
| *A61K 45/06* | (2006.01) | |
| *A61K 9/00* | (2006.01) | |

(52) U.S. Cl.
CPC ............. *A61K 31/728* (2013.01); *A61K 9/0053* (2013.01); *A61K 31/138* (2013.01); *A61K 31/198* (2013.01); *A61K 31/401* (2013.01); *A61K 45/06* (2013.01)

(58) Field of Classification Search
CPC ..................................................... A61K 31/198
See application file for complete search history.

(56) References Cited

U.S. PATENT DOCUMENTS

| | | | |
|---|---|---|---|
| 2005/0256042 A1 * | 11/2005 | Jeffers et al. | 514/12 |
| 2008/0287392 A1 * | 11/2008 | Conti | 514/54 |
| 2009/0274660 A1 | 11/2009 | Girsh | |

FOREIGN PATENT DOCUMENTS

| | | |
|---|---|---|
| WO | 02/39978 A1 | 5/2002 |
| WO | 2007/048524 A2 | 5/2007 |
| WO | 2008/027904 A2 | 3/2008 |

OTHER PUBLICATIONS

ISR and Written Opinion issued in PCT/EP2010/068216.

* cited by examiner

*Primary Examiner* — Scott Long
*Assistant Examiner* — Sarah Alawadi
(74) *Attorney, Agent, or Firm* — Silvia Salvadori, P.C.; Silvia Salvadori

(57) ABSTRACT

The present invention relates to the use of a combination of glycine, proline, and optionally a natural or synthetic film-forming polymer, and/or lysine and/or leucine, to prepare a composition for the treatment of mucositis induced by radiation or chemotherapy.

7 Claims, No Drawings

COMBINATION FOR THE TREATMENT OF RADIATION- OR CHEMOTHERAPY-INDUCED MUCOSITIS

This utility Application is the continuation of U.S. Ser. No. 13/511,900 which was filed on Aug. 1, 2012, which is U.S. national stage of International Application PCT/EP2010/068216 which was filed on Nov. 25, 2010 and which claims priority to and the benefit of Italian Application No. MI2009A002080 filed on Nov. 26, 2009, the contents of which are incorporated herein by reference in their entirety.

The present invention relates to a combination of glycine, proline and optionally a natural or synthetic film-forming polymer, and/or lysine and/or leucine, for the treatment of mucositis induced by radiation or chemotherapy.

TECHNICAL BACKGROUND

Oral mucositis (OM) is one of the most frequent and potentially serious side effects of non-surgical antitumoral treatment (1,2). Clinically, it is characterised by erythema, formation of ulcers with or without pseudo-membranes, bleeding, formation of exudates, and/or infections located at the upper level (3), and can evolve into a debilitating form which adversely affects the patient's quality of life. The damage to the mucous membranes can extend from the oral cavity to the pharynx; in this invention, therefore, the term "oral mucositis" includes mucositis of the pharynx.

The patient's perception of the symptoms associated with OM ranges from a sensation of pain in the mouth to impairment of various oral functions (4). OM can be associated with pain symptoms such as dysgeusia, dysphagia, and difficulty in speaking, chewing or swallowing, with consequent impairment of the ability to eat, weight loss, and the need for feeding through a nasogastric tube.

All this not only has an adverse impact on the patient's quality of life, but can also lead to discontinuance of the treatment or a reduction in the dose of antitumoral medicament, with a consequent decline in the patient's life expectancy (5). In financial terms, the frequent hospital admissions of patients suffering from OM, and their home care by personnel skilled in the administration of drugs or parenteral feeding, involve a considerable burden on the national health service (6,7).

Despite the severity and frequency of cases of OM and the many studies conducted on the subject, there is still no universally accepted standard strategy for the prevention and treatment of this potentially serious complication. Although some trials have demonstrated that the onset of OM can be prevented or reduced, they were conducted on an insufficient number of participants, and do not meet adequate standards which allow the drafting of clinical practice guidelines (8-11).

At present, the treatment of OM and the pain caused by it comprises: basic topical anaesthetics, systemic analgesics, anti-inflammatories, mucosa-coating agents, mouthwashes, oral hygiene in general, and antimicrobials (5,12-15). A number of other agents have also been tested, such as growth factors and cytokines, biological compounds that protect the mucosa, cryotherapy, and low-level laser treatment (13,16). Hyaluronic acid (HA) plays an important role in tissue healing, by means of various mechanisms (17-19); clinical trials have also confirmed that it improves the healing process of ulcers of the lower limbs (20) and the nasal mucosa after surgery (21) and reduces acute epithelitis in patients who undergo radiotherapy to treat head, neck, breast or pelvic cancer (22).

The research therefore focuses on new treatment strategies for oral mucositis and the corresponding formulations.

It was recently demonstrated that a gel based on 0.2% HA for topical use not only relieves the pain/stinging associated with recurrent aphthous stomatitis and atrophic/erosive oral lichen planus, but also contributes to the clinical resolution of areas presenting ulcers, erosions or atrophy (23,24).

WO 2007/048524 describes wound-healing pharmaceutical compositions comprising a combination of glycine, lysine, leucine and proline and sodium hyaluronan, which is particularly effective in facilitating the process of cell renewal that forms the basis of rapid wound-healing, promoting connective tissue reconstruction and consequent regeneration of the epithelial cells.

WO 2008/027904 discloses formulations of viscous polymers such hyaluronates or PVPs for treating stomatitis or mucositis. WO 02/39978 discloses enteral nutritional supplement for malnourished or chronically ill patients comprising glutamine, anti-oxidants and fatty acids. Glycine can be optionally present as a calcium antagonist.

DESCRIPTION OF THE INVENTION

It has now been discovered that combinations comprising glycine, proline, and optionally a natural or synthetic film-forming polymer, lysine and/or leucine, are effective in the treatment of oral mucositis induced by radiation or chemotherapy, especially as regards pain management. In particular, it has been found that the combination of glycine and proline surprisingly increases the gene expression of e-NO Synthase and of VEGF. Moreover, said aminoacids control and enhance the production of TGF beta and controls the collagen synthesis by fibroblasts quantitatively. This means that the combination of glycine and proline, peculiarly when in association with lysine and leucine, is also efficient in suppressing TGF beta expression and thus prevents fibrotic collagen production when the rate of collagen production by fibroblasts is maximal. Hyaluronic acid alone has absolutely no activity in this respect, and thus no prevention of fibrotic scarring can be observed and obtained.

The compositions according to the present invention have a considerable accelerating effect on wound-healing, and above all a surprising effect on pain management, especially in terms of pain reduction and immediate relief (only 2 hours after administration). The use of the compositions according to the invention therefore constitutes a practical aid to pain management, providing rapid, effective pain reduction.

The present invention therefore relates to a formulation for oral use comprising:
a) glycine,
b) proline,
and optionally
c) a natural or synthetic film-forming polymer, and/or
d) lysine, and/or
e) leucine,
for the treatment of oral mucositis induced by radiation or chemotherapy.

According to the invention, the natural or synthetic film-forming polymer is selected from hyaluronic acid or a salt thereof, polyvinylpyrrolidone, and cellulose derivatives.

According to a preferred aspect, the natural or synthetic film-forming polymer is hyaluronic acid or a salt thereof.

According to the invention, the aminoacids are present in the L form. According to a preferred aspect, the compositions according to the invention will contain the various active constituents in the following proportions of the composition by weight:

a) 0.5 to 20% of glycine,
b) 0.2 to 15% of proline,
and optionally
c) 0.5 to 5% of hyaluronic acid or a salt thereof, and/or
d) 0.05 to 10% of lysine, and/or
e) 0.05% to 3% of leucine.

The compositions according to the invention could be formulated suitably for topical administration in the form of a spray, aerosol, mouthwash or gel, and will be prepared according to conventional methods well known in pharmaceutical technology, such as those described in Remington's Pharmaceutical Handbook, Mack Publishing Co., N.Y., USA, using excipients, solubilisers, emollients, stabilisers, emulsifiers, pH regulators and preservatives acceptable for their final use.

Pharmacological Tests

The trial was conducted on 27 patients with OM, who had been treated recently (within two weeks) with daily doses of radiotherapy or chemotherapy, who presented at least grade 1 OM as assessed on the World Health Organisation (WHO) mucositis scale, and whose pain was not alleviated by treatment with paracetamol/co-codamol/acetylsalicylic acid. Each patient was treated 3-4 times a day for 14 days with the composition according to the invention in spray form, which had to be maintained in situ for at least 2 minutes. They were instructed not to eat, drink or rinse their mouths for at least 1 hour. Throughout the trial period, the patients were asked to take particular care with their oral hygiene, using mouth rinses comprising a non-alcoholic solution of chlorhexidine gluconate, and not to smoke, drink alcohol or eat irritant foods. The results of the trial are illustrated in Tables I and II below.

Table I shows the pain score at the various assessment stages. At time T0 (baseline—before start of treatment), the following parameters were assessed: pain (using a linear visual analog scale from 1 to 100) and gravity of OM (using the WHO mucositis scale). The efficacy of the treatment was assessed on the basis of the pain score, the clinical resolution index and patients' compliance at times T01 (after 2 hours), T1 (after 24 hours), T2 (after 72 hours), T3 (after 7 days) and T4 (after 14 days).

TABLE I

Pain score evaluated with VAS at the various assessment stages.

| Pain score | Mean (mm) ± SD | Intra-group test (Wilcoxon test) | Intra-group test in repeated measures models (Friedman test) |
|---|---|---|---|
| Pain T0 (baseline) | 74.1 (±17.6) | Significant differences at T01 ($p < 0.0001$) and after 24 h, 72 h, 7 and 14 days ($p < 0.0001$) compared with baseline | ($p < 0.0001$) |
| Pain T01 (after 2 h) | 49.3 (±18.2) | | |
| Pain T1 (after 24 h) | 39.4 (±22) | | |
| Pain T2 (after 72 h) | 24.8 (±19) | | |
| Pain T3 (after 7 days) | 11.8 (±15.5) | | |
| Pain T4 (after 14 days) | 6.2 (±10.8) | | |

The results showed a significant reduction in pain symptoms only 2 hours after administration of the spray, by comparison with the baseline measurements ($p<0.0001$; $z=-4.541$). This pain reduction progressed during the two-week period ($p<0.0001$).

Table II shows the effect of the treatment on the clinical resolution index. The treated patients exhibited a significant clinical improvement in the lesions only 72 hours after the treatment ($p=0.0051$; $z=-2.803$; Wilcoxon test). In particular, the Friedman test showed a significant clinical improvement ($p<0.0001$) compared with baseline at the various stages of measurement. During the two-week observation period, all patients showed a significant improvement compared with baseline ($p<0.0001$), and their ability to swallow solids and liquids gradually improved.

TABLE II

Effect on clinical resolution index during treatment.

| Stages of measurement | Clinical Resolution Index | Number of patients (%) |
|---|---|---|
| T1 (after 24 hours) | Complete | 1 (3.7) |
| | Partial | 14 (51.9) |
| | Absent | 12 (44.4) |
| T2 (after 71 hours) | Complete | 3 (11.1) |
| | Partial | 20 (74.1) |
| | Absent | 4 (14.8) |
| T3 (after 7 days) | Complete | 5 (18.5) |
| | Partial | 22 (81.5) |
| | Absent | 0 (0) |
| T4 (after 14 days) | Complete | 21 (77.8) |
| | Partial | 6 (22.2) |
| | Absent | 0 (0) |

All the patients also exhibited good compliance, and none of them complained of side effects at the end of the trial. None of the patients was obliged to discontinue the radiotherapy or chemotherapy treatment.

REFERENCES

1. Scully C, Sonis S, Diz PD. Oral mucositis. Oral Dis 2006; 12:229-241.
2. Scully C, Epstein J, Sonis S. Oral mucositis: a challenging complication of radiotherapy, chemotherapy, and radio-chemotherapy: part 1, pathogenesis and prophylaxis of mucositis. Head Neck 2003; 25:1057-1070.
3. Compilato D, Cirillo N, Termine N, Kerr A R, Paderni C, Ciavarella D, Campisi G. Long-standing oral ulcers: proposal for a new "S-C-D classification system". J Oral Pathol Med 2009; 38:241-253.
4. Scully C, Epstein J, Sonis S. Oral mucositis: a challenging complication of radiotherapy, chemotherapy, and radio-chemotherapy. Part 2: diagnosis and management of mucositis. Head Neck 2004; 26:77-84.
5. Saadeh C E. Chemotherapy- and radiotherapy-induced oral mucositis: review of preventive strategies and treatment. Pharmacotherapy 2005; 25:540-554.
6. Peterman A, Cella D, Glandon G, Dobrez D, Yount S. Mucositis in head and neck cancer: economic and quality-of-life outcomes. J Natl Cancer Inst Monogr 2001:45-51.
7. Elting L S, Cooksley C, Chambers M, Cantor S B, Manzullo E, Rubenstein E B. The burdens of cancer therapy. Clinical and economic outcomes of chemotherapy-induced mucositis. Cancer 2003; 98:1531-1539.
8. Rubenstein E B, Peterson D E, Schubert M, Keefe D, McGuire D, Epstein J, Elting L S, Fox P C, Cooksley C, Sonis S T. Clinical practice guidelines for the prevention and treatment of cancer therapy-induced oral and gastrointestinal mucositis. Cancer 2004; 100:2026-2046.
9. Worthington H V, Clarkson J E, Eden O B. Interventions for preventing oral mucositis for patients with cancer receiving treatment. Cochrane Database Syst Rev 2007: CD000978.

10. Clarkson J E, Worthington H V, Eden O B. Interventions for treating oral mucositis for patients with cancer receiving treatment. Cochrane Database Syst Rev 2007: CD001973.
11. Potting C, Mistiaen P, Poot E, Blijlevens N, Donnelly P, van Achterberg T. A review of quality assessment of the methodology used in guidelines and systematic reviews on oral mucositis. J Clin Nurs 2009; 18:3-12.
12. Epstein J B, Schubert M M. Oropharyngeal mucositis in cancer therapy. Review of pathogenesis, diagnosis, and management. Oncology (Williston Park) 2003; 17:1767-1779; discussion 1779-1782, 1791-1762.
13. Bensadoun R J, Le Page F, Darcourt V, Bensadoun F, Ciais G, Rostom Y A, Poissonnet G, Dassonville O, Demard F. [Radiation-induced mucositis of the aerodigestive tract: prevention and treatment. MASCC/ISOO mucositis group's recommendations]. Bull Cancer 2006; 93:201-211.
14. Bensinger W, Schubert M, Ang K K, Brizel D, Brown E, Eilers J G, Elting L, Mittal B B, Schattner M A, Spielberger R, Treister N S, Trotti A M 3rd. NCCN Task Force Report. Prevention and management of mucositis in cancer care. J Natl Compr Canc Netw 2008; 6 Suppl 1: 51-21; quiz S22-24.
15. Lalla R V, Sonis S T, Peterson D E. Management of oral mucositis in patients who have cancer. Dent Clin North Am 2008; 52:61-77.
16. Arora H, Pai K M, Maiya A, Vidyasagar M S, Rajeev A. Efficacy of He—Ne Laser in the prevention and treatment of radiotherapy-induced oral mucositis in oral cancer patients. Oral Surg Oral Med Oral Pathol Oral Radiol Endod 2008; 105:180-186.
17. Chen W Y, Abatangelo G: Functions of hyaluronan in wound repair. Wound Repair Regen 1999; 7:79-89.
18. Price R D, Berry M G, Naysaria H A. Hyaluronic acid: the scientific and clinical evidence. J Plast Reconstr Aesthet Surg 2007; 60:1110-1119.
19. David-Raoudi M, Tranchepain F, Deschrevel B, Vincent J C, Bogdanowicz P, Boumediene K, Pujol J P. Differential effects of hyaluronan and its fragments on fibroblasts: relation to wound healing. Wound Repair Regen 2008; 16:274-287.
20. Ortonne J P. [Comparative study of the activity of hyaluronic acid and dextranomer in the treatment of leg ulcers of venous origin]. Ann Dermatol Venereol 2001; Suppl: 13-16.
21. Soldati D, Rahm F, Pasche P. Mucosal wound healing after nasal surgery. A controlled clinical trial on the efficacy of hyaluronic acid containing cream. Drugs Exp Clin Res 1999; 25:253-261.
22. Liguori V, Guillemin C, Pesce G F, Mirimanoff R O, Bernier J. Double-blind, randomized clinical study comparing hyaluronic acid cream to placebo in patients treated with radiotherapy. Radiother Oncol 1997; 42:155-161.
23. Nolan A, Badminton J, Maguire J, Seymour R A. The efficacy of topical hyaluronic acid in the management of oral lichen planus. J Oral Pathol Med 2009; 38:299-303.
24. Nolan A, Baillie C, Badminton J, Rudralingham M, Seymour R A. The efficacy of topical hyaluronic acid in the management of recurrent aphthous ulceration. J Oral Pathol Med 2006; 35:461-465.

The invention claimed is:
1. A method of treating oral mucositis induced by radiation or chemotherapeutics with an oral formulation consisting of:
   a) glycine,
   b) proline,
   c) a natural or synthetic film-forming polymer,
   d) lysine, or leucine and
   e) pharmaceutically acceptable excipients thereof.
2. The method as claimed in claim 1, wherein the natural or synthetic film-forming polymer is selected from hyaluronic acid or a salt thereof, polyvinylpyrrolidone and cellulose derivatives.
3. The method as claimed in claim 2, wherein the natural or synthetic film-forming polymer is hyaluronic acid or a salt thereof.
4. The method as claimed in claim 2, wherein proline and lysine are in the L form.
5. The method as claimed in claim 1, wherein the various components of the combination are present in the following composition ranges by weight:
   a) 0.5 to 20% of glycine,
   b) 0.2 to 15% of proline,
   c) 0.5 to 5% of hyaluronic acid or a salt thereof,
   d) 0.05 to 10% of lysine, or 0.05% to 3% of leucine.
6. The method as claimed in claim 1, wherein the composition is in the form of a spray, aerosol, mouthwash or gel.
7. The method as claimed in claim 2, wherein proline and leucine are in the L form.

* * * * *